United States Patent [19]
Thanner

[11] Patent Number: 4,878,505
[45] Date of Patent: Nov. 7, 1989

[54] ANKLE SUPPORTING SLEEVE

[76] Inventor: Arthut Thanner, Am Fallenweg 30, D-8884, Höchstädt/Donau, Fed. Rep. of Germany

[21] Appl. No.: 238,393

[22] Filed: Aug. 30, 1988

[30] Foreign Application Priority Data

Sep. 1, 1987 [DE] Fed. Rep. of Germany ....... 3729197

[51] Int. Cl.[4] .......................................... A61F 13/00
[52] U.S. Cl. .................................. 128/882; 128/166
[58] Field of Search ............. 2/2, 22; 128/166, 166.5; 36/89, 90

[56] References Cited

U.S. PATENT DOCUMENTS

| | | | |
|---|---|---|---|
| 757,816 | 4/1904 | Krieger | 36/89 |
| 1,081,366 | 12/1913 | Collis | 128/166 |
| 1,231,332 | 6/1917 | Collis | 128/166 |
| 1,548,172 | 8/1925 | Redden | 36/89 |
| 1,586,698 | 6/1926 | Posner | 36/89 |
| 2,165,879 | 7/1939 | Wilkinson | 128/166 |
| 3,028,861 | 4/1962 | Shapiro | 36/89 |

Primary Examiner—Robert A. Hafer
Assistant Examiner—Charles H. Sam
Attorney, Agent, or Firm—Christie, Parker & Hale

[57] ABSTRACT

This invention relates to an ankle supporting sleeve (1) having side parts (2,2') in which receiving pockets (10, 11 and 10', 11') are incorporated. These receiving pockets (10, 11, 10', 11') each feature an insertion opening (12, 13 and 12', 13') provided with a releasable fastener (14, 14'). Reinforcing parts can be introduced into said receiving pockets (10, 11 and 10', 11') thus making it possible to adapt the sleeve to various applications and the time of treatment optimally.

12 Claims, 2 Drawing Sheets

ANKLE SUPPORTING SLEEVE

BACKGROUND OF THE INVENTION

This invention relates to an ankle supporting sleeve having side reinforcing parts in receiving pockets.

One such ankle supporting sleeve is illustrated in U.S. Pat. No. 1,084,197. This supporting sleeve features receiving pockets for reinforcing parts which comprise straight rods. Accordingly the receiving pockets are also formed straight and extend over an area of the side parts which run over the ankle when the ankle supporting sleeve is worn. This represents a first disadvantage of one such supporting sleeve since even when cushioned it cannot be sufficiently prevented that the reinforcing parts exert an unwanted and uncomfortable pressure on the ankle.

In addition, said supporting sleeve features over the complete front longitudinal edge above the insertion opening a hard edging on all sides, from which, to make the situation worse, the closing straps are folded inwards, thus resulting in choking of the foot and in further unwanted points of pressure.

The object of the present invention is thus to create a supporting sleeve permitting flexible adaptation of an optimized therapeutical supporting effect to the malady in each case and advancement of the healing process whilst simultaneously affording high wearing comfort, it being intended to devise said ankle supporting sleeve for utilization in commercially-available shoes.

SUMMARY OF THE INVENTION

The invention relates to an ankle supporting sleeve comprising:
  two side parts;
  a rear connecting part connecting said side parts by their longitudinal edges;
  a releasable fastener located on the opposite front longitudinal edges of said side parts;
  a lower connecting part connecting said side parts by each of their bottom edges; and
  rod-shaped reinforcing parts each located in corresponding receiving pockets in each side part
  wherein the receiving pockets extend along the longitudinal edges and each feature an insertion opening provided with a releasable fastener
  wherein the receiving pockets merge in an acute angle, wherein the insertion openings are arranged in the area of the apex of the angle
  wherein the receiving pockets located on the outside are considerably longer than the receiving pockets located on the inside of the foot
  wherein the removable reinforcing parts exhibit a slight curvature and can be of differing hardness, shape and longitudinal expansion, and
  wherein the upper formed by the side parts and by the connecting part is provided with a cushioned U-shaped extension part having an upper material which is softer and more flexible than that of the upper.

In the first instance this provides a considerable improvement of the adaptation to the anatomical features of the ankle, since the ankle does not come into contact with the reinforcing parts when the supporting sleeve is worn, thus reliably preventing uncomfortable pressure points.

At the same time, unwanted choking of the foot and painful pressure points are prevented, despite a high side supporting effect being achieved by the specific arrangement of the receiving pockets and the therein accommodated reinforcing parts.

The supporting sleeve as the object of the present invention thus makes it particularly easy and advantageous to achieve the wanted side supporting effect without restricting movement of the foot in directions in which no supporting effect is necessary. This makes the supporting sleeve as the object of the present invention useful for numerous applications which was not satisfactorily achievable by other existing supporting sleeves.

One particular advantage afforded by the supporting sleeve as the object of the present invention is the possibility of adjusting the supporting effect of the sleeve, when worn, to the injury being treated, further advantages also including the fact that the supporting sleeve can be worn day and night and in combination with practically every form of a usual shoe. In addition, when the material is selected accordingly, the supporting sleeve can also be worn when wetting of the foot with water is unavoidable, as in, for instance, acquatic sports.

Furthermore, it is a welcome aspect from a medical point of view when the ankle in the final stages of the healing process can become reaccustomed to stressing to an extent which is at least approximative to that when no supporting sleeve is worn. Successively reducing the supporting force in this way is possible to an optimum degree by the supporting sleeve as the object of the present invention, since it can be provided with reinforcing parts of differing strength, depending on the nature of the injury involved, when the healing process is still in its initial stages, and since it is even possible, when the ankle has practically regained normal health, to remove all of the reinforcing parts so that the supporting effect results solely from the inherent rigidity of the upper of the supporting sleeve.

The sub-claims constitute further advantageous embodiments of the invention.

When only one fastener for each two receiving pockets is provided, this has the advantage that the design is simplified and also, weight is saved.

Providing cushioned pads also has the advantage that comfort is not detrimented even when relatively hard reinforcing parts are utilized.

Comfort is also considerably enhanced by providing ventilation openings.

When the fastener covers part of the front longitudinal edges, this has the advantage that unwanted choking of the foot can be prevented without restricting movement of the foot up or down relative to the shank despite affording high side support.

Configuring the fastener as a laced fastener featuring full or semi-round eyelets respresents a particularly advantageous embodiment whereas a burr-type fastener is of advantage since the sleeve can be closed and opened single-handedly with no problem.

The special arrangement and connection of trapezoidally shaped panel parts and of a connecting strap is of particular advantage in that they assist in preventing choking of the foot and, in addition, enable the weight and size of the supporting sleeve to be further reduced.

Arranging for the length of the connecting strap to be roughly 30% of the length of the lower edge constitutes, as a last advantage, a configuration which is particularly favourable from an anatomical point of view, creating—especially in combination with the advantageous embodiment wherein the front fastener is located towards the upper end of the front longitudinal edges—particularly favourable conditions for movement of the foot in conjunction with a high supporting effect, whilst eliminating unwanted choking of the foot.

BRIEF DESCRIPTION OF THE DRAWINGS

Some embodiments of the invention will now be described by way of example and with reference to the accompanying drawings in which.

DESCRIPTION OF THE PREFERRED EMBODIMENT

Figure 1:
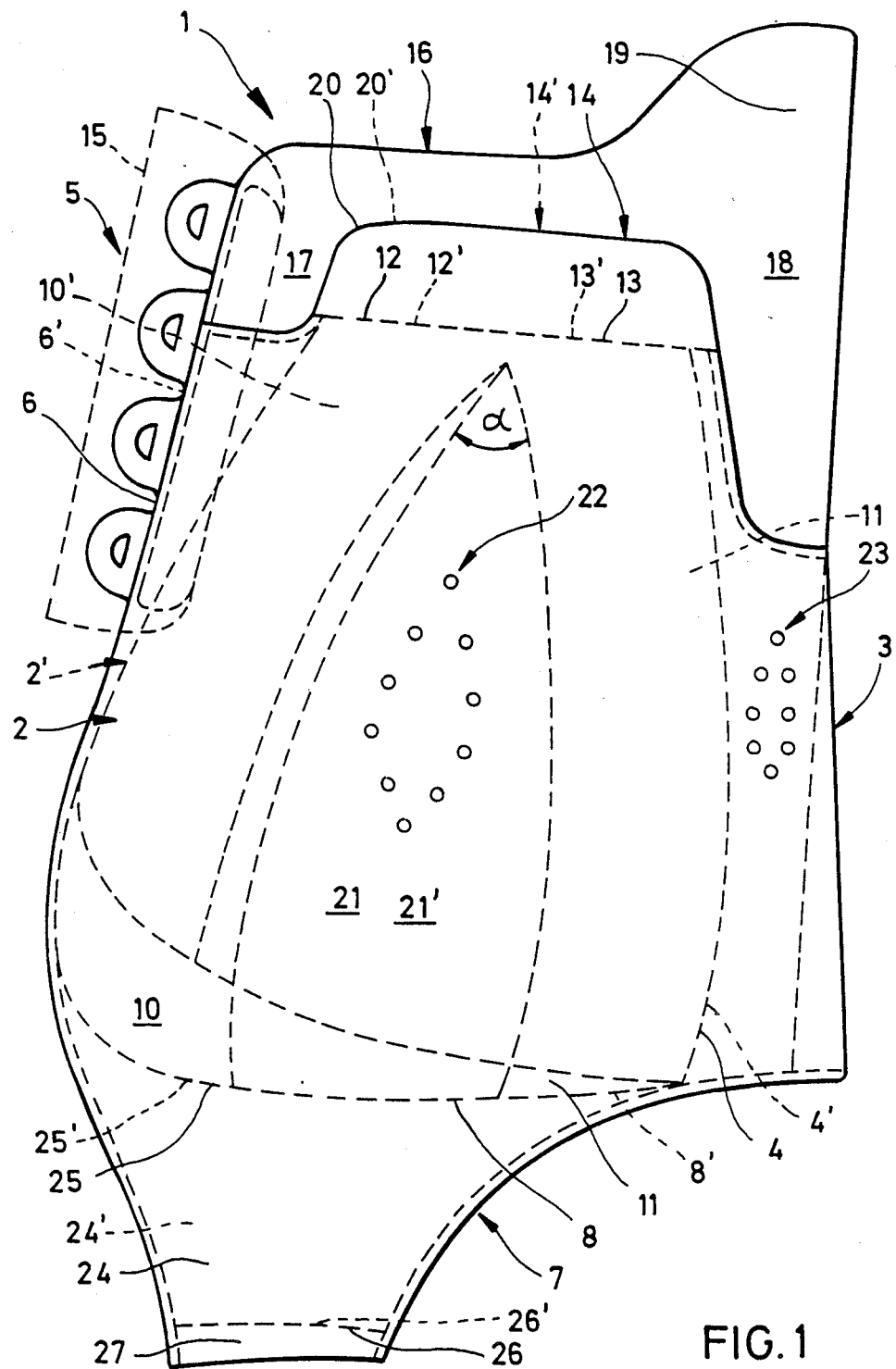
FIG. 1 is a side-view of an ankle supporting sleeve as the object of the invention.

FIG. 1 illustrates an ankle supporting sleeve 1 as the object of the invention in compressed condition, so that its two side parts 2, 2' are located one on the other, and in which, to some extent, merely the top side part 2 is visible. Since the plane of the drawing represents the dividing plane of the supporting sleeve 1 and since the parts located on both sides of this dividing plane are, with few exceptions, identical, the parts not shown in the drawing are each identified by the same numbers, but indexed.

The two side parts 2,2' are connected together by a rear connecting part 3 adjoining their rear longitudinal edges 4, 4', FIG. 1 showing only half of said connecting part 3 due to the illustration selected. Said connecting part 3 itself is shown as a single item and, by way of example, attached to the rear longitudinal edges 4, 4' of the side parts 2, 2' by stiching. It is, however, possible to also form side parts 2,2' and connecting part 3 as a single item.

On the opposite front longitudinal edge 6 or 6' of the side part 2 or 2' a fastener 5 is provided. Said fastener takes the form of a laced fastener in the embodiment as shown in FIG. 1. In this example it features eight half-round lacing eyelets in an arrangement of four each on every longitudinal edge 6, 6'. Through said eyelets a lace can be threaded, this lace is not shown in FIG. 1. The fastener as illustrated in FIG. 1 also shows a tongue 15 which is cushioned-padded as indicated by the dotted lines.

The two side parts 2,2' are also connected together at their lower edges 8, 8' by means of a connecting part 7 which is described in more detail in the following.

It can also be seen from FIG. 1 that the illustrated embodiment features two receiving pockets 10 and 11 or 10' and 11' each in the side part 2 or 2'. These have insertion openings 12 and 13 or 12' and 13' at the top edge, as shown in the drawing, said openings in turn featuring a releasable fastener 14 or 14'. FIG. 1 makes it clear that when sleeve 1 is worn, the receiving pocket 10 arranged on the outside is considerably longer than the corresponding front receiving pocket 10' of side part 2', this applying just the same to the rear receiving pockets 11 and 11', although the difference in length in this case is somewhat less.

Figure 2:
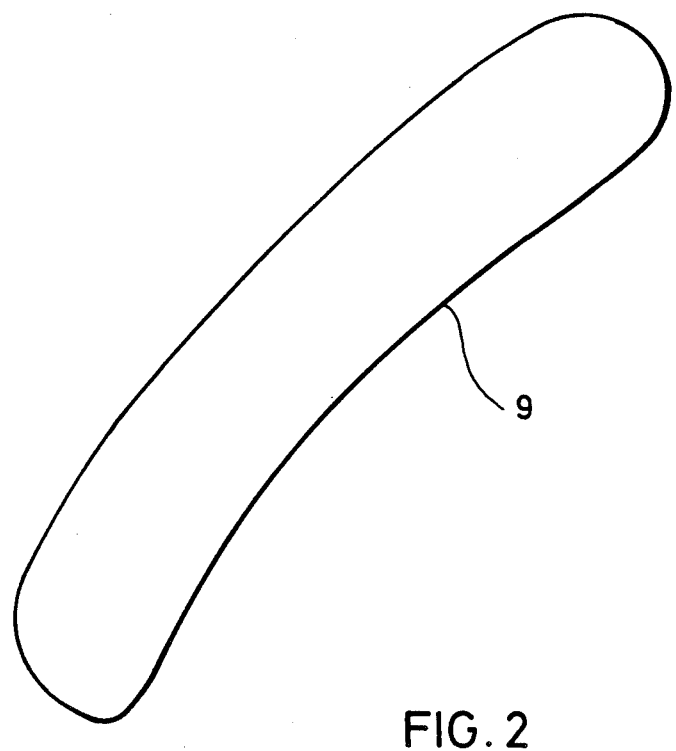
FIG. 2 is a side-view of a reinforcing part.

Reinforcing parts 9 can be embodied in the receiving pockets 10, 11, 10', 11' cut to size accordingly, one of which is depicted schematically slightly simplified in FIG. 2. It can be seen from this Figure that the reinforcing part 9 is preferrably configured rod-shaped and featuring both a slight curvature and rounded corners. The reinforcing part 9 can be produced of different materials of differing hardness, thermoplastic moldable materials in particular receiving most preference. The differing shape and length of the receiving pockets 10, 10' and 11, 11' and the accordingly differing configuration of the reinforcing part 9 result in the advantage of further improving the ability of the supporting sleeve to adapt to different foot shapes and thus helping to prevent pressure points.

Although FIG. 1 shown an embodiment of the supporting sleeve 1 with a total of four receiving pockets 10, 11, 10', 11' it is also possible to provide fewer receiving pockets. Furthermore it is also possible to embody a differing number of reinforcing parts 9 in the existing receiving pockets to adapt the sleeve to different stages of treatment and/or applications. It is, therefore, possible that every receiving pocket 10, 11, 10', 11' is occupied by a corresponding reinforcing part 9; conversely it is also possible that none of the receiving pockets 10, 11, 10', 11' will be occupied by a reinforcing part 9 so that the supporting effect is then generated merely by the inherent rigidity of the upper formed by the side parts 2, 2' and the connecting part 3.

In the embodiment of the supporting sleeve 1 shown in FIG. 1 the upper is also provided with an extension part 16 which is essentially U-shaped, and which in the area of the fasteners is joined to these, wherein the two sections 17 and 18 of said extension piece differ in length, section 18 also featuring an upswept extension section 19.

The aforementioned side parts 2, 2', the connecting part 3, the connecting part 7 as well as the part 16 comprise upper and lining material which is preferably quilted , cushioned padding being incorporated between the upper material and the lining material to prevent pressure points. In this respect the upper material of part 16 is preferably formulated softer than the upper material of the remaining aforementioned parts to achieve enhanced flexibility of part 16. In addition, the lining material of parts 3 and 16 can be a single piece. Leather or a wipe-clean synthetic material akin to leather can be used in general as the material.

As can be seen also from FIG. 1, the receiving pockets 10, 11, 10', 11' extend along the longitudinal edges 4, 4' or 6,6' respectively and merge in an acute angle α whereby the insertion openings 12, 12' and 13, 13' are arranged in the area of this angle α. This results in the avantage that only one fastener 14 or 14' is required for two each pockets 10, 11 or 10', 11', said fastener enabling both pockets 10, 11 or 10', 11' to be opened and closed. In the embodiment shown in FIG. 1 the fastener 14 or 14' takes the form of a burr-type fastener. This fastener features a swivelling strap 20 or 20', the inside surface of which has a burr-type lining which acts together with a burr-type surface on the outside of part 16.

As an alternative, fastener 14, 14' can also be provided as a zip fastener which has the advantage of further reducing the thickness of sleeve 1.

As already mentioned, cushioned padding is incorporated between the upper and lining materials of the supporting sleeve 1 which is configured thicker in the area of the receiving pockets than in the area between the receiving pockets as identified 21 and 21'. This results in the particular advantage of improving the strain-relief on the ankle, the wearing comfort being further enhanced by providing numerous ventilation openings 22 in the area 21, 21'. The rear connecting part 3 can also be provided with ventilation openings of this kind as identified by 23. FIG. 1 also illustrates that the fastener 5 is located only above the upper portion of the longitudinal edges 6 or 6' so that the merging portion of the supporting sleeve 1 in the instep of the foot is not held together even when the fastener is closed. This offers the particular advantage of effectively preventing choking of the foot and, in addition, improving freedom of movement of the foot whilst maintaining a high supporting effect. In addition to this, there is the further advantage that the supporting sleeve 1 as the object of the invention, takes up practically no room in the area of the foot which is covered up by the parts of the shoe when worn, thus enabling all kinds of shoes to be worn when the sleeve is applied.

These advantageous effects are further enhanced in the embodiment of the supporting sleeve shown in FIG. 1 by the lower connecting part 7 featuring two approximately trapezoidal panel parts 24 and 24', each of which is connected to the bottom edges 8 or 8' by their longer sides 25 or 25'. The shorter sides 26 or 26' are connected together by a connecting strap 27. This strap is essentially rectangular shaped and preferably has a length corresponding to roughly a third of the length of the bottom edge 8 or 8'. This results in the configuration of the area of the supporting sleeve 1, shown in detail in FIG. 1, which covers the sole of the foot when the sleeve 1 is worn. In conjunction with the fastener 5 this results in particularly advantageous conditions producing, at the same time, maintenance of a high supporting effect together with major freedom of movement of the foot whilst avoiding the risk of choking the foot. All in all, the ankle supporting sleeve 1 as the object of the present invention creates a supporting device which can be used in particular to support weak ligaments and in preventive and post-operative applications. In addition it can be used to advantage in practically any kind of shoe and is particularly suitable for applications in which especially the ankle-joint is exposed to exceptional stress.

As illustrated in FIG. 1 the reinforcing parts 9 are upswept sufficiently over the ankle-joint to ensure an optimum side support whilst guaranteeing high freedom of movement due to the embodiment of the fastener 5, as described above, in conjunction with the connecting part 7 which leaves the heel free.

As another embodiment the supporting sleeve 1 can take the form of an ankle-joint and mid-food bandage having essentially the same configuration as the foregoing sleeve, except that it also surrounds the mid-foot section and features side movement nicks in the bend. This makes the sleeve 1 especially suitable in healing ligaments injuries, following plaster cast removal and for strain-relief and immobilizing the ankle-joint.

A further advantage of the supporting sleeve 1 as the object of the invention, particularly with regards to shoes, is that only a single sleeve need be purchased and worn when merely one foot has been injured and, furthermore, that the sleeve can also be worn during the night without being a nuisance.

In addition, it is also possible for arch-supports to be worn in addition to the supporting sleeve 1 since the sleeve is configured relatively narrow and small particularly in the area of the sole, thus eliminating the fear of excessive impediments even when the shoe is worn.

I claim:

1. Ankle supporting sleeve comprising:
   two side parts each having an inner surface and an outer surface;
   a rear connecting part connecting said side parts by their rear longitudinal edges to from a main portion of the sleeve;
   a releasable front fastening means for releasably connecting the opposite front longitudinal edges of said side parts;
   a lower connecting part connecting said side parts by each of their bottom edges; and
   front and rear elongated receiving pockets defined between the inner and outer surfaces of each side part, each of the receiving pockets adapted to receive a corresponding elongated, slightly curved reinforcing part, wherein
   the front and rear receiving pockets are slightly curved and extend along the corresponding respective front and rear longitudinal edges and each defines an insertion opening extending through the outer surface of its respective side part and provided with a releasable pocket fastening means for releasably closing its associated insertion opening,
   top portions of the front and rear receiving pockets merge at each side to from an acute angle,
   the insertion openings are located in the vicinity of the acute angle,
   the front and rear receiving pockets located on one of the side parts are considerably longer than the correspond front and rear receiving pockets located on other of the two side parts,
   the removable reinforcing parts exhibit a slight curvature,
   at least one of the reinforcing parts differs from another of the reinforcing parts in at least one physical characteristic selected from the group consisting of hardness, curvature and flexibility,
   the side parts and the connecting part are provided with an cushioned U-shaped extension part which extends above said main portion, and
   at least an outer surface of the U-shaped extension part is formed from a material which is softer and more flexible than the corresponding materials forming the outer surfaces of the main portion of the supporting sleeve.

2. An ankle supporting sleeve as claimed in claim 1, wherein a unitary said pocket fastening means is provided for the front and rear receiving pockets on each of the side parts.

3. An ankle supporting sleeve as claimed in claim 1, wherein the respective inner surfaces of the side parts are provided with cushioning in the vicinity of said receiving pockets.

4. An ankle supporting sleeve as claimed in claim 3, wherein an area of the inner surface of the side part between the front and rear receiving pockets is provided with a cushioned pad which is thinner than the cushioning in the vicinity of the receiving pockets.

5. An ankle supporting sleeve as claimed in claim 4, wherein each of the side parts is provided with ventilation openings between the front and rear receiving pockets.

6. An ankle supporting sleeve as claimed in claim 1, wherein the rear connecting part is provided with ventilation openings.

7. An ankle supporting sleeve as claimed in claim 1, wherein the front fastening means extends only over part of the front longitudinal edges, starting from their upper end.

8. An ankle supporting sleeve as claimed in claim 1, wherein the front fastening means comprises a fastener selected from the group consisting of laced fasteners and burr-type fasteners.

9. An ankle supporting sleeve as claimed in claim 1, wherein the lower connecting part features two approximately trapezoidally-shaped panel sections, each of which is connected by their longer sides to the lower edges, whilst the shorter sides are connected together by an essentially rectangular connecting strap.

10. An ankle supporting sleeve as claimed in claim 9, wherein the length of the connecting strap corresponds to roughly 30% of the length of the lower edge.

11. An ankle supporting sleeve as claimed in claim 1, wherein the pocket fastening means comprises a fastener selected from the group consisting of burr-type fasteners and zip fasteners.

12. An ankle supporting sleeve as claimed in claim 1, wherein the reinforcing parts comprise a thermoplastic moldable material.

* * * * *

UNITED STATES PATENT AND TRADEMARK OFFICE
CERTIFICATE OF CORRECTION

PATENT NO. : 4,878,505

DATED : November 7, 1989

INVENTOR(S) : Arthur Thanner

It is certified that error appears in the above-identified patent and that said Letters Patent is hereby corrected as shown below:

On the Front Page:

[76] Inventor, change "Arthut Thanner" to
-- Arthur Thanner --.

In the Specification

Column 2, line 45, change "detrimented" to
-- sacrifice --.
Column 2, line 55, change "respresents" to
-- represents --.

Column 3, line 33, change "stiching" to -- stitching --.
Column 3, line 65, change "preferrably" to
-- preferably --.

Column 4, line 8, change "shown" to -- shows --.
Column 4, line 32, move the comma to come directly after "quilted".

Column 5, line 5?, change "ligaments" to -- ligament --.

UNITED STATES PATENT AND TRADEMARK OFFICE
CERTIFICATE OF CORRECTION

PATENT NO. : 4,878,505

DATED : November 7, 1989

INVENTOR(S) : Arthur Thanner

It is certified that error appears in the above-identified patent and that said Letters Patent is hereby corrected as shown below:

```
Column 6, line 2, change "from" to -- form --.
Column 6, line 22, change "from" to -- form --.
Column 6, line 27, change "correspond" to
          -- corresponding --.
Column 6, line 36, before "cushioned" change "an" to
          -- a --.
```

Signed and Sealed this

Seventeenth Day of September, 1991

Attest:

HARRY F. MANBECK, JR.

*Attesting Officer*       *Commissioner of Patents and Trademarks*